United States Patent [19]

Vanstone et al.

[11] 4,190,671
[45] Feb. 26, 1980

[54] CHALCONE DERIVATIVES

[75] Inventors: Anthony E. Vanstone, Whitton; Graham K. Maile, Harlow, both of England

[73] Assignee: Biorex Laboratories Limited, London, England

[21] Appl. No.: 883,252

[22] Filed: Mar. 3, 1978

[30] Foreign Application Priority Data

Mar. 17, 1977 [GB] United Kingdom ............... 11339/77
Aug. 26, 1977 [GB] United Kingdom ............... 35925/77

[51] Int. Cl.$^2$ .................. C07C 65/22; A61K 31/19; C07C 65/20
[52] U.S. Cl. .................. 424/317; 562/463; 562/464; 260/343.3 R; 260/507 R; 424/279; 260/511
[58] Field of Search .................. 562/464; 424/317

[56] References Cited

U.S. PATENT DOCUMENTS

| | | | |
|---|---|---|---|
| 3,255,241 | 6/1966 | Schultz et al. | 562/431 |
| 3,928,421 | 12/1975 | Kyogoku et al. | 560/138 |
| 3,956,375 | 5/1976 | Farkas et al. | 562/464 |
| 3,994,955 | 11/1976 | Sprenger | 562/464 |
| 4,085,135 | 4/1978 | Kyogoku et al. | 562/464 |

*Primary Examiner*—Natalie Trousof
*Assistant Examiner*—Jane T. Fan
*Attorney, Agent, or Firm*—Wenderoth, Lind & Ponack

[57] ABSTRACT

The present invention provides new chalcone derivatives of the general formula:

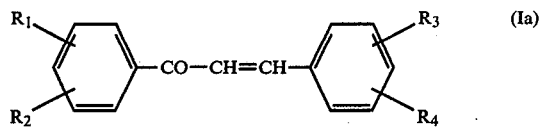

and

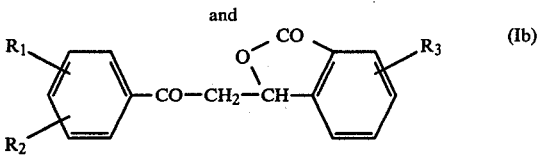

wherein $R_1$ is a hydroxyl, carboxylic acid or sulphonic acid group or a carboxyalkoxy or sulphoalkoxy radical, $R_2$ and $R_3$, which may be the same or different, are hydrogen or halogen atoms, hydroxyl groups or alkoxy radicals and $R_4$ is an alkyl, hydroxyalkyl, alkoxy, carboxyalkoxy, sulphoalkoxy or carboxyalkylcarbonyloxyalkyl radical or a carboxylic acid or sulphonic acid group, with the proviso that compounds of general formula (Ia) always contain at least one carboxylic acid or sulphonic acid group; and the non-toxic inorganic and organic salts of those compounds containing at least one carboxylic acid or sulphonic acid group, the compounds of the invention are useful for treating inflammatory and allergic conditions and for treating ulcerous conditions of the gastro-intestinal tract in humans.

13 Claims, No Drawings

CHALCONE DERIVATIVES

BACKGROUND OF THE INVENTION

In spite of the large number of known pharmaceutically-active compounds for the treatment of inflammatory and allergic conditions, as well as for the treatment of ulcerous conditions of the gastro-intestinal tract, there is a need for new compounds for treating these indications which are less toxic than the known compounds and/or which are more effective than the known compounds. It is an object of the present invention to provide such new compounds.

SUMMARY OF THE INVENTION

Thus, the present invention provides new chalcone derivatives of the general formulae:

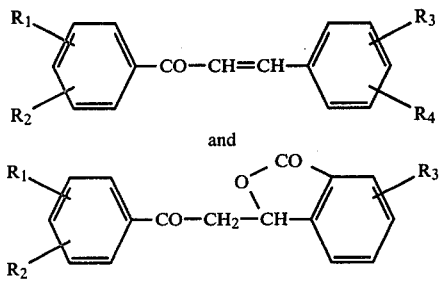

wherein $R_1$ is a hydroxyl, carboxylic acid or sulphonic acid group or a carboxyalkoxy or sulphoalkoxy radical, $R_2$ and $R_3$, which may be the same or different, are hydrogen or halogen atoms, hydroxyl groups or alkoxy radicals and $R_4$ is an alkyl, hydroxyalkyl, alkoxy, carboxyalkoxy, sulphoalkoxy or carboxyalkylcarbonyloxyalkyl radical or a carboxylic acid or sulphonic acid group, with the proviso that compounds of general formula (Ia) always contain at least one carboxylic acid or sulphonic acid group; and the non-toxic inorganic and organic salts of those compounds containing at least one carboxylic acid or sulphonic acid group.

DETAILED DESCRIPTION OF THE INVENTION

It is to be expected that the ethylenic double bond of the new chalcone derivatives (Ia) is in the more thermodynamically stable *trans* form.

Carboxyalkoxy radicals $R_1$ and $R_4$ are preferably of the formula $-O-(CH_2)_n-COOH$ in which n is an integer equal to or greater than 1 and is preferably 1 to 3.

The alkyl, hydroxyalkyl and alkoxy radicals constituting or forming part of substituents in the new compounds according to the present invention preferably contain up to 6 carbon atoms and more preferably contain up to 3 carbon atoms.

The new compounds according to the present invention can be prepared, for example, by condensing an acetophenone derivative of the general formula:

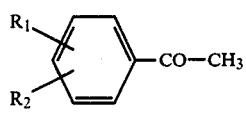

in which $R_1$ and $R_2$ have the same meanings as above, with an aldehyde of the general formula:

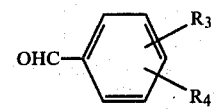

in which $R_3$ and $R_4$ have the same meanings as above.

This condensation reaction is preferably carried out in the presence of a strong base, for example an alkali metal hydroxide, in an aqueous or aqueous organic medium.

The reaction can be carried out at a temperature between ambient temperature and the boiling point of the reaction mixture.

When a product is obtained in which $R_4$ is a hydroxyalkyl radical, this can, if desired, be subsequently reacted with an appropriate reactive derivative of an alkane-dicarboxylic acid to give the corresponding carboxyalkylcarbonyloxyalkyl compound.

When $R_4$ is a carboxyl group in the o-position, the product can, if desired, be subsequently lactonised to give a compound of general formula (Ib).

Since the product obtained contains at least one free carboxylic or sulphonic acid group, this can, if desired, be subsequently reacted with a non-toxic inorganic or organic base to give the corresponding salt.

The following Examples are given for the purpose of illustrating the present invention:

EXAMPLE 1

(a) 50 g. m-Toluic acid were dissolved in 750 ml. methanol and 15 ml. concentrated sulphuric acid added thereto. The reaction mixture was refluxed for 3 hours, whereafter thin layer chromatography (petroleum ether/dichloromethane/acetone 6:3:1 v/v/v) showed esterification to be complete. The solution was reduced to ⅓ volume on a rotary evaporator, diluted with water and extracted with chloroform. The organic extract was washed with aqueous sodium bicarbonate solution to remove any acid and then with water until the aqueous washings were neutral. The extract was then dried with anhydrous sodium sulphate. Removal of solvent gave an almost colourless oil which was distilled under water pump pressure to yield a major fraction (b.p. 120°–121° C./14 mm.Hg). Yield 48.1 g. methyl m-toluate. The product was pure by thin layer chromatography and the infra-red spectrum showed ester absorption but no acid absorption.

(b) 32.7 g. methyl m-toluate were placed in a 1 liter round bottomed flask equipped with a mechanical stirrer. To this were added 340 ml. glacial acetic acid and then 339 ml. acetic anhydride, the reaction mixture being finally cooled to 0° C. (ice/salt bath). 51 ml. concentrated sulphuric acid were added slowly, ensuring that the temperature did not exceed 6° C., the addition taking approximately 2 hours. When all the acid had been added, the reaction mixture was again cooled to 0° C. and 60 g. chromium trioxide were added in small portions, making sure that the temperature did not rise above 5° C. When addition was complete, the reaction mixture was allowed to warm to 10° C. for 10 minutes and then poured into 2.5 liters ice-water. The resultant mixture was allowed to stand for 30 minutes, then filtered, washed with water and pressed dry to give 25.8 g. material after final drying. This crude product was finely ground and thoroughly mixed with 200 ml. 2% aqueous sodium carbonate solution. The undissolved material was filtered off, washed with water and dried in a vacuum oven at 60° C. to give 20.8 g. 3-carbomethoxybenzaldiacetate which was not further purified. Thin layer chromatography indicated that the product had a purity greater than 99%.

(c) 23.8 g. 3-Carbomethoxybenzaldiacetate, 50 ml. ethanol, 50 ml. distilled water and 5 ml. concentrated sulphuric acid were refluxed on a water-bath for 1 hour. The reaction mixture was then diluted with 300 ml. water and extracted with diethyl ether. The organic extract was washed with water, aqueous sodium bicarbonate solution and finally with water until the washings were neutral. The extract was dried with anhydrous sodium sulphate, filtered and the filtrate evaporated to give an almost colourless oil. This was dried in a vacuum desiccator for a further 2 hours. Yield of methyl 3-formylbenzoate 11.40 g. The oil solidified on standing at ambient temperature to give a white solid. Thin layer chromatography (petroleum ether/dichloromethane/acetone 6:3:1 v/v/v) showed the product to be more than 99% pure. The material had a melting point of 51°–53° C.

(d) 20.5 g. 4-Hydroxyacetophenone, 25 g. methyl 3-formylbenzoate, 250 ml. ethanol and 250 ml. 10% aqueous sodium hydroxide solution were stirred at 50° C. for 4 hours. Thin layer chromatography (9:1 chloroform/methanol+1% acetic acid) then indicated that the condensation had gone to completion. The reaction mixture was allowed to cool and then left at ambient temperature overnight. Careful acidification with concentrated hydrochloric acid yielded a pale yellow solid which was filtered off, washed well with water until the washings were neutral and then dried in a vacuum oven at 100° C. This yielded 22.9 g. 3-carboxy-4'-hydroxychalcone. Thin layer chromatography and gas liquid chromatography both indicated that the material was at least 99% pure. The compound had a melting point of 273°–276° C.

EXAMPLE 2

16.32 g. 4-Hydroxy-acetophenone (m.p. 111°–113° C.), 18.0 g. 4-carboxy benzaldehyde (m.p. 245°–247° C.), 180 ml. ethanol and 180 ml. 10% aqueous sodium hydroxide solution were stirred at 60° C. for 5 hours. The reaction mixture was allowed to cool and then left at ambient temperature overnight. Careful acidification with concentrated hydrochloric acid yielded a pale yellow solid which was filtered off, washed once with ethanol and then with water until the washings were neutral. The solid was dried to constant weight on a steam bath (yield 23.6 g.), dissolved in hot methanol/chloroform, filtered and the solution boiled down to about 400 ml. and left to cool overnight. The resulting pale yellow solid was filtered, washed with methanol and dried in a vacuum oven at 80° C. (yield 13.3 g.). Thin layer chromatography (chloroform/methanol/acetic acid 89:10:1 v/v/v) and gas liquid chromatography (5' 1% OV-17, t=240° C.) both indicated the material to be at least 99% pure. The 4-carboxy-4'-hydroxy chalcone thus obtained had a melting point of 300°–301.5° C.

EXAMPLE 3

(a) A solution of 8.8 g. sodium hydroxide and 11.35 g. chloroacetic acid (20% excess) in 110 ml. distilled water was added to 13.6 g. 4-hydroxy acetophenone and the resultant solution was refluxed on an oil bath with magnetic stirring for 8.5 hours. At regular intervals, the pH was measured and kept in the 8–9 range by the further addition of aqueous sodium hydroxide solution as necessary. Thin layer chromatography (petroleum ether/dichloromethane/acetone 6:3:1 v/v/v) showed the reaction to be approximately 60% complete but reflux was discontinued as no further progress was being made. The hot reaction mixture was acidified with an excess of concentrated hydrochloric acid and the white solid filtered off, washed with water and dried (yield=12.45 g.). This product was dissolved in 5% aqueous sodium carbonate solution and washed several times with ethyl acetate. The aqueous layer was then acidified with hydrochloric acid and the solid filtered off, washed with water and dried (yield=10.2 g.). This material was crystallised from ethyl acetate to give 9.8 g. of crystalline 4-carboxymethoxy-acetophenone which was shown to be 99% pure by thin layer chromatography (chloroform/methanol/acetic acid 89:10:1 v/v/v). The material had a melting point of 183°–185° C.

(b) 7.76 g. 4-Carboxymethoxy-acetophenone and 4.80 g. m-tolualdehyde were placed in a 250 ml. round-bottomed flask equipped with a magnetic stirrer and a reflux condenser and heated on an oil bath. 50 ml. ethanol and 50 ml. aqueous 10% sodium hydroxide solution were added and the stirred mixture heated to 30° C., whereupon the mixture solidified. A thin layer chromatogram showed the reaction to have proceeded about 70%. 100 ml. ethanol/water (1:1) were added and the mixture was heated to 60° C. and thoroughly shaken for 15 minutes. Upon cooling, crystallisation took place and the solid was filtered off, washed with a little water and sucked dry. This was then crystallised from methanol containing 10% of a 1% aqueous solution of sodium carbonate. The white crystalline needles were filtered off, washed with a little water, washed thoroughly with diethyl ether and dried in a vacuum at 70° C. Yield 7.0 g. A second crop of 1.6 g. was obtained from the mother liquors. Thin layer chromatography (n-butanol/ammonia 10:1 v/v) showed the product to be more than 99% pure. Gas chromatography (5' 1% OV-17 column at 240° C.) also showed better than 99% purity. The sodium salt of 4'-carboxymethoxy-3-methyl-chalcone thus obtained had a melting point of 315°–318° C.

EXAMPLE 4

15.52 g. 4-Carboxymethoxy acetophenone and 12.00 g. 4-carboxy-benzaldehyde were dissolved in 70 ml. 10% aqueous sodium hydroxide solution and left at ambient temperature for 16 hours. An equal volume of methanol was added and the precipitated solid filtered off, washed thoroughly with methanol and dried. (Yield=23.8 g.). This material was dissolved in the minimum of hot water (120 ml.) and an equal volume of methanol added. Crystallisation took place and, when cold, the product was filtered off, washed thoroughly with methanol and dried to constant weight. Yield 13.8 g. disodium salt of 4-carboxy-4'-carboxymethoxy-chalcone. Thin layer chromatography (ethyl acetate/methanol/30% triethylamine 70:20:40 v/v/v) showed the material to be more than 99% pure; m.p. >360° C.

A sample of the disodium salt was converted into the free acid which had a melting point of 313°–314° C.

EXAMPLE 5

(a) To 24.4 g. 4-hydroxy benzaldehyde was added a solution of 17.6 g. sodium hydroxide and 22.7 g. chloroacetic acid in 150 ml. distilled water and the resultant solution was refluxed. After one hour, the pH of the solution had dropped to 7 and a further 1 g. of sodium hydroxide was added. After a further 2 hours refluxing, another 1 g. of sodium hydroxide was added. Thin layer chromatography (chloroform/methanol/acetic acid 89:10:1) showed the reaction to be about 80% complete so refluxing was continued for a further 2 hours. The hot solution was acidified with concentrated hydrochloric acid and crystallisation took place upon cooling. The solid was filtered off, washed with water and dried: yield 22.2 g. This material was crystallised from ethyl acetate and then from chloroform/methanol. Yield 11.6 g. 4-carboxymethoxybenzaldehyde, which was more than 99% pure by thin layer chromatography. The product had a melting point of 203°–204° C.

(b) 9.75 g. 4-Carboxymethoxy-acetophenone and 9.0 g. 4-carboxymethoxy-benzaldehyde were dissolved in 100 ml. 5% aqueous sodium hydroxide solution and left for 16 hours at ambient temperature. A solid which had precipitated was filtered off, washed thoroughly with methanol and dried to constant weight; yield 18.0 g. This material was dissolved in 230 ml. water, filtered off and an equal volume of methanol added. Crystallisation took place and the solid was filtered off, washed with methanol and dried; yield 14.0 g. This purification was repeated to give 11.8 g. material. Thin layer chromatography (ethyl acetate/methanol/30% triethylamine 70:20:40 v/v/v) showed the product to be more than 99% pure. The disodium salt of 4,4'-di-(carboxymethoxy)-chalcone thus obtained had a melting point of 275°–276° C.

EXAMPLE 6

15.52 g. 4-Carboxymethoxy acetophenone and 13.1 g. methyl 3-formyl benzoate were dissolved in 80 ml. aqueous 10% sodium hydroxide solution, left at ambient temperature for 16 hours and then heated to 50° C. for 30 minutes. An equal volume of methanol was added and the precipitated solid was filtered off, washed thoroughly with methanol and dried; yield 18.4 g. This material was dissolved in the minimum of hot water and the clear solution was diluted to 200 ml. with methanol. Crystallisation took place and, when cold, the product was filtered off, washed thoroughly with methanol and dried to constant weight; yield 12.1 g. Thin layer chromatography (ethyl acetate/methanol/30% trimethylamine 70:20:40 v/v/v) showed the material to be more than 99% pure. The disodium salt of 3-carboxy-4'-carboxymethoxy-chalcone thus obtained had a melting point of >360° C. The water content was found to be 4.9% (Karl Fischer) and a 1:1 compound/water molar ratio would give a water content of 4.64%. Since further drying at 110° C. under water pump vacuum did not reduce the water content, the product probably contains one molecule of water of crystallisation.

A sample of this disodium salt was converted into the free acid. The melting point of the diacid was 296°–298° C. (with decomposition).

EXAMPLE 7

(a) A solution of 220 g. ceric ammonium nitrate (technical grade) in 250 ml. distilled water was prepared at 38° C. and one half thereof added to 27.6 g. finely ground benzene-1,4-dimethanol and the mixture swirled. As reaction occurred, the temperature rose to 57° C. and the dark colour disappeared. The remainder of the oxidant was added in portions, keeping the temperature just below 60° C. When the reaction was complete, the reaction mixture was cooled, neutralised with aqueous 10% sodium hydroxide solution and filtered. The solution was extracted with two 125 ml. portions of petroleum ether (b.p. 60°–80° C.)/diethyl ether (4:1) and the aqueous layer then extracted with three portions of chloroform. The chloroform extracts were combined, washed once with a saturated aqueous solution of sodium bicarbonate, dried over anhydrous sodium sulphate, filtered, evaporated in a rotary evaporator and dried; yield 18.5 g. This material was crystallised from toluene in a refrigerator to give 12 g. of white crystals of 4-formyl-benzyl alcohol, which was shown to be 99% pure by thin layer chromatography. The product had a melting point of 39°–41° C.

(b) To a mixture of 8.16 g. 4-formyl-benzyl alcohol and 11.64 g. 4-carboxymethoxy acetophenone was added 150 ml. aqueous 5% sodium hydroxide solution and the solution was stirred at ambient temperature. A solid precipitated and after 10 minutes the mixture became too thick to stir so a further 50 ml. of aqueous 5% sodium hydroxide solution were added. After stirring for 3 hours, the reaction mixture was left to stand overnight. The solid was filtered off, washed three times with aqueous 5% sodium hydroxide solution, boiled with 300 ml. methanol, filtered off, washed with methanol and dried; yield 18.0 g. This material was dissolved in 200 ml. hot water and the solution was filtered, boiled down to about 140 ml. and allowed to cool. The solid obtained was filtered off, washed with methanol and dried; yield 9.3 g. Thin layer chromatography (ethyl acetate/methanol/30% trimethylamine 7:2:4 v/v/v) showed the material to be more than 99% pure. The monosodium salt of 4'-carboxymethoxy-4-hydroxymethyl-chalcone thus obtained had a melting point of >360° C. (decomposition from about 326° C.). The corresponding free acid had a melting point of 203°–204° C.

EXAMPLE 8

(a) 30 g. 3-Fluoro-4-methoxyacetophenone were dissolved in 250 ml. dry benzene. In a separate vessel, a solution of 115 g. aluminium bromide in 350 ml. benzene was prepared. This solution was filtered to remove insoluble impurities and then added to the above solution. When the initial exothermic reaction had ceased, the reaction mixture was refluxed for 2 hours. After this time, thin layer chromatography indicated that the reaction was complete.

The reaction mixture was worked up by pouring carefully, with stirring, into 300 ml. ice/water. When all the mixture had been quenched, the resultant two-layer mixture was poured into a separating funnel and 200 ml. ethyl acetate added thereto. The organic layer was washed three times with water, dried over anhydrous sodium sulphate and evaporated in a rotary evaporator to give 20.8 g. of a pale yellow solid. This solid was dissolved in the minimum amount of ethyl acetate and treated with charcoal. The solution thus obtained was reduced in volume to about 50 ml. by boiling, then 100 ml. benzene were added thereto and the solution again reduced to 50 ml. Upon cooling, the material crystallised. It was filtered off, washed twice with benzene and dried in vacuo at 70° C. to give 19.6 g. of colourless crystalline 3-fluoro-4-hydroxyacetophenone, which was shown to be pure by thin layer chromatography; m.p. 130°–132° C.

18 g. 3-Fluoro-4-hydroxyacetophenone were dissolved in a solution of 11.5 g. sodium hydroxide in 200 ml. water. To the solution were added 12.5 g. chloroacetic acid and the mixture then refluxed. The reaction mixture was allowed to reflux for 2 hours, whereafter thin layer chromatography indicated that a 60% reaction had taken place. The pH of the solution was also checked and found to be low (about 7). 0.5 g. Sodium hydroxide was, therefore, added to the reaction mixture and refluxing continued for 10 hours. Thin layer chromatography after this time showed that the reaction had still only proceeded to 60% so the reaction mixture was worked up.

The reaction mixture was cooled to ambient temperature and extracted three times with ethyl acetate to remove starting material for recycling. The aqueous layer was acidified to pH 1 with concentrated hydrochloric acid and the precipitated solid collected, washed three times with water and dried in vacuo at 70° C. to give 14.05 g. of a pale yellow solid which was shown by thin layer chromatography to be 96–97% pure.

The material was dissolved in ethyl acetate, treated with charcoal and filtered. Upon reducing the volume of the filtrate, crystallisation occurred. The crystals were filtered off, washed with cold ethyl acetate and dried in vacuo at 70° C. to give 10 g. of a colourless, crystalline solid which was shown to be more than 99% pure by thin layer chromatography. The 3-fluoro-4-carboxymethoxy acetophenone thus obtained had a melting point of 170°–172° C.

(b) 10 g. 3-Fluoro-4-carboxymethoxy acetophenone and 7.1 g. 4-carboxybenzaldehyde were dissolved in 10% aqueous sodium hydroxide solution. Rapid solution was assured by stirring vigorously and after about 90 seconds the reaction mixture solidified.

The solid was left to stand overnight and the following day it was heated to 60° C. for one hour. While still hot, 200 ml. methanol were added, with stirring, to the reaction mixture and the resultant slurry allowed to cool. When cool, the precipitated product was collected, washed with methanol and dried in vacuo at 60° C. to give 13.6 g. of a yellow solid.

This solid was redissolved in the minimum of water and filtered. To the still hot solution was then carefully added sufficient methanol to precipitate all the product (about four to five times the quantity of water).

When cool, the solid material was collected, washed with methanol and dried in vacuo at 60° C. to give 10.1 g. of a pale yellow crystalline material which was shown to be pure by thin layer chromatography. The disodium salt of 4-carboxy-3'-fluoro-4'-carboxymethoxy chalcone thus obtained had a melting point of >350° C.

EXAMPLE 9

10 g. 3-Fluoro-4-hydroxyacetophenone and 9.4 g. 4-carboxybenzaldehyde were dissolved in 120 ml. 10% aqueous sodium hydroxide solution and dissolved by vigorously stirring. The reaction mixture was left overnight and on the following morning heated to 60° C. for 1 hour. The reaction mixture was then cooled and acidified to pH 1 with concentrated hydrochloric acid. The precipitated solid was collected, washed well with water and dried in vacuo at 70° C. to give 15.1 g. of a pale yellow solid.

This solid was recrystallised from chloroform/methanol (1:4) to give a crystalline, pale yellow product which was washed with cold methanol and dried in vacuo at 60° C. to give 10.1 g. 4-carboxy-3'-fluoro-4'-hydroxychalcone.

This product was shown to be pure by thin layer chromatography; m.p. 272°–274° C. (decomp.).

EXAMPLE 10

(a) 16.3 g. 4'-Carboxymethoxy-4-hydroxymethyl chalcone (see Example 7) and 6.27 g. succinic anhydride were dissolved in 50 ml. anhydrous pyridine and the solution was heated on a water-bath for 90 minutes. A thin layer chromatogram showed the reaction to be complete. The cold reaction mixture was poured into ice-water/hydrochloric acid (excess) and the precipitated solid was filtered off, washed with water until neutral and dried; yield = 21.0 g. This material was charcoaled and crystallised from chloroform/methanol and the filtered solid washed with methanol and dried; yield = 17.2 g. Thin layer chromatography showed an impurity to be still present which was not removed by further crystallisations so column chromatography was carried out as follows: 16.5 g. of the material were dissolved in chloroform/methanol, 33 g. silica gel 60 were added and the mixture was evaporated to dryness. This was placed on a dry silica column (660 g.) and eluted with chloroform/methanol (8:2) containing 1% acetic acid. The pure fractions were combined, evaporated and dried. Yield = 14.7 g. 4'-carboxymethoxy-4-$\beta$-carboxypropionylmethyl-chalcone, which had a melting point of 190°–192° C. Gas chromatography showed the material to be more than 99% pure.

(b) 12.44 g. 4'-Carboxymethoxy-4-$\beta$-carboxypropionyloxymethyl chalcone were finely ground and slurried with 20 ml. distilled water. The suspension was magnetically stirred and 30 ml. aqueous 10% sodium carbonate solution were added dropwise. The rate of addition was slowed down towards the end as the reaction became slower. The cloudy solution obtained was filtered and acetone added until precipitation was complete. The solid was filtered off, washed with acetone and dried to constant weight; yield 12.2 g. Thin layer chromatography showed the material to be more than 99% pure. The disodium salt of 4'-carboxy-methoxy-4-$\beta$-carboxypropionyloxymethyl-chalcone thus obtained had a melting point of >360° C. (with decomposition from 333° C.).

EXAMPLE 11

(a) 32.4 g. sodium hydroxide and 41.9 g. chloroacetic acid were dissolved in 368 ml. distilled water. This solution was added to 50 g. 3-hydroxyacetophenone and the resultant solution was refluxed on an oil bath. After a reaction period of 3 hours, the pH of the solution was found to be about 6. A further 2 g. of sodium hydroxide were added to bring the pH up to about 9 and the solution then heated under reflux for a further 8 hours. Thin layer chromatography on the cooled reaction mixture (pH 8) indicated that about 80% reaction had occurred and the reaction mixture was worked up in the following manner: The reheated reaction mixture was acidified dropwise with concentrated hydrochloric acid and the precipitated solid filtered, washed thoroughly with water and dried in a vacuum oven at 80° C.; yield 54.9 g. The solid was dissolved in 5% aqueous sodium carbonate solution and washed several times with ethyl acetate. The aqueous basic layer was acidified, washed with water and dried in a vacuum oven at 80° C.; yield 46.8 g. The crude product was dissolved in hot ethyl acetate, charcoaled, concentrated and left to crystalline at 0° C. A white crystalline solid was obtained. Yield of 1st crop material 29.0 g.; yield of 2nd crop material 5.0 g. The 3-carboxymethoxyacetophenone thus obtained had a melting point of 121°–123° C.

(b) 15.52 g. 3-Carboxymethoxyacetophenone, 13.1 g. 4-carboxybenzaldehyde and 80 ml. 10% aqueous sodium hydroxide solution were mixed in a 250 ml. conical flask and stirred at ambient temperature for 30 seconds. After this very brief period, the reaction mixture had solidified. Thin layer chromatography of a sample indicated that approximately 90% reaction had occurred. The reaction product was heated and stirred on a water bath for 5 minutes and 100 ml. methanol added. The mixture was stirred and heated for a further 10 minutes and then cooled. The solid was filtered off, washed with methanol and dried in a vacuum oven to constant weight; yield 26.0 g. This was then dissolved in a minimum volume of hot water (about 175 ml.), filtered through a No. 44 paper and methanol added (about 350 ml.) until precipitation occurred. The resultant mixture was cooled to ambient temperature, with stirring, and then kept at 0° C. overnight. Filtration gave yellow crystals which were washed well with methanol and dried in a vacuum oven to constant weight; yield of 1st crop material 17.2 g. Thin layer chromatography indicated that the product was pure. The disodium salt of 4-carboxy-3'-carboxymethoxy-chalcone thus obtained had a melting point of >360° C.

EXAMPLE 12

15.52 g. 4-Carboxymethoxyacetophenone and 9.60 g. p-tolualdehyde were placed in a 500 ml. round-bottomed flask equipped with a magnetic stirrer and reflux condenser. To this was added 100 ml. of a 5% aqueous sodium hydroxide solution and the resulting mixture was stirred at ambient temperature until precipitation occurred. A further 50 ml. of 5% aqueous sodium hydroxide solution were added and the reaction mixture stirred for 2 hours at ambient temperature. After this period of time, thin layer chromatography indicated that an approximately 50% reaction had taken place. After the addition of a further 50 ml. of 5% aqueous sodium hydroxide solution, the reaction mixture was heated to 60° C. for 30 minutes, whereafter a thin layer chromatogram showed the complete absence of starting materials. The reaction mixture was finally cooled and the precipitated solid was filtered off, washed with water and pressed dry. The solid was dissolved in hot water/methanol (2:1) containing 500 mg. sodium carbonate and filtered hot. Concentration and cooling yielded, after filtration and washing with water, 14 g. of first crop material as a white solid. This was the monosodium salt of 4-methyl-4'-carboxymethoxy-chalcone. Thin layer chromatography indicated that the product was more than 99% pure. The compound had a melting point of >360° C. The corresponding free acid had a melting point of 196°–197° C.

EXAMPLE 13

17.46 g. 4-Carboxymethoxy acetophenone and 13.5 g. recrystallised 2-carboxy-benzaldehyde were dissolved in 75 ml. 10% aqueous sodium hydroxide solution, warming to about 50° C. being required. After 45 minutes at ambient temperature, a thin layer chromatogram showed incomplete reaction. The reaction mixture was warmed to 50° C. for 4 hours and left at ambient temperature overnight. The precipitated product was filtered off, washed with a little methanol and then washed thoroughly with I.M.S. After drying in a vacuum oven at 80° C., 20.1 g. of product were obtained. Thin layer chromatography showed this material to be 98% pure. It was finely ground, slurried with 30 ml. methanol containing 1 pellet of sodium hydroxide, filtered, thoroughly washed with I.M.S. and dried; yield 18.4 g. Thin layer chromatography showed this material to be more than 99% pure. The pH of a 10% aqueous solution was found to be 9.8. After a further I.M.S. wash, the pH of a 10% aqueous solution was found to be 7.2. The product had a melting point of >360° C. It was the expected disodium salt of 2-carboxy-4'-carboxymethoxy-chalcone.

EXAMPLE 14

(a) To 24.4 g. 3-hydroxybenzaldehyde were added a solution of 17.6 g. sodium hydroxide and 22.7 g. chloroacetic acid in 150 ml. distilled water and the resultant solution heated under reflux for 1 hour. The pH of the solution was measured and found to be about 8 so a further 1 g. sodium hydroxide was added. Reflux was continued and the pH checked periodically, sodium hydroxide being added in 1 g. quantities when required. The total reaction time was 8 hours, whereafter the pH was 9 and a thin layer chromatogram showed that about 80% reaction had taken place. The reaction mixture was left to cool overnight and then washed with ethyl acetate to remove starting material until the washings were colourless. Careful acidification with concentrated hydrochloric acid gave a brownish coloured precipitated which was filtered, washed well with water and dried to constant weight in a vacuum oven; yield 21.6 g. of crude material.

The crude product was crystallised from ethyl acetate to give 17.8 g. of 1st crop material in the form of pale buff coloured crystals. Thin layer chromatography indicated that this material was more than 99% pure. The product, which had a melting point of 124°–126° C., was 3-carboxymethoxy-benzaldehyde.

(b) To 10.8 g. 3-carboxymethoxybenzaldehyde and 11.64 g. 4-carboxymethoxyacetophenone were added, with continual stirring, 60 ml. of 10% aqueous sodium hydroxide solution. The reaction mixture was stirred for 30 minutes at ambient temperature and then left at ambient temperature for 1 hour, during which time a yellow solid precipitated out. Since a thin layer chromatogram indicated that there was only a very small quantity of starting material left, the reaction mixture was worked up by diluting with 60 ml. methanol, filtering, washing the filtered solid with methanol and drying to constant weight in a vacuum oven. Yield 17 g. A second batch of material (7 g.) from another experiment and showing identical T.L.C. characteristics was combined with the above batch and the resulting batch (24 g.) dissolved in 100 ml. hot water. 200 ml. methanol were added and crystallisation occurred upon cooling. The crystals were filtered off, washed well with methanol and dried to constant weight in a vacuum oven. Yield of 1st crop material 13.3 g.

Thin layer chromatography indicated that the material was more than 99% pure. The compound had a melting point of >350° C. and a pH of 7.6 (10% solution). The compound was the expected disodium salt of 3,4'-dicarboxymethoxy chalcone.

EXAMPLE 15

15 g. of the disodium salt of 2-carboxy-4'-carboxymethoxy-chalcone (see Example 13) were dissolved in 250 ml. distilled water, acidified with concentrated hydrochloric acid to pH 1 and the resulting suspension heated to 60° C. on a water-bath for 30 minutes. The white precipitate was washed several times with water until the washings were neutral and then dried in a vacuum oven at 50° C. Yield 13.39 g. This product was combined with the product from a similar lactonisation experiment to give a total of 22.6 g.

The crude lactone was dissolved in 600 ml. ethyl acetate/methanol (2:1 v/v) with stirring and heating. The cloudy solution was filtered and concentrated until crystallisation occurred. The white precipitate was filtered off, washed with ethyl acetate and dried to constant weight in a vacuum oven at 50° C. Yield of 1st crop material 20.5 g. Thin layer chromatography indicated that the first crop material was pure. An NMR spectrum indicated that there was methanol present, probably as solvent of crystallisation. Further drying in a vacuum oven at 110° C. successfully removed this.

The product obtained, which was 2-carboxy-4'-carboxymethoxy-chalcone γ-lactone, had a melting point of 184°–186° C.

EXAMPLE 16

15.52 g. 4-Carboxymethoxyacetophenone and 10.88 g. 3-methoxybenzaldehyde were slurried in 40 ml. methanol. 40 ml. 10% aqueous sodium hydroxide solution were added thereto, with vigorous stirring, and stirring then continued until a clear solution was obtained.

The reaction mixture was left to stand at ambient temperature for 5 hours, whereafter thin layer chromatography showed that an approximately 70% reaction had occurred. The reaction mixture was heated to 60° C. to redissolve the precipitated solid and the mixture left for a further 2 hours, after which time thin layer chromatography showed that 80% reaction had taken place.

The reaction mixture was cooled and the solid product filtered off, washed twice with cold methanol and dried to constant weight in a vacuum oven at 70° C. 18.1 g. of a pale yellow amorphous solid were obtained. This solid was dissolved in 100 ml. water at 70°–80° C., filtered and the filtrate left to cool. Crystallisation took place and the crystals were filtered off, washed twice with cold water and dried to constant weight in a vacuum oven at 70° C. 17.2 g. of a pale yellow crystalline solid were obtained. This was the sodium salt of 3-methoxy-4'-carboxymethoxy chalcone; m.p. 283°–285° C. Thin layer chromatography showed the product to be more than 99% pure.

EXAMPLE 17

15.52 g. 4-Carboxymethoxy-acetophenone (see Example 3) and 10.88 g. p-anisaldehyde were mixed with 85 ml. methanol and 85 ml. 10% aqueous sodium hydroxide solution and the reaction mixture heated under reflux for 3 hours. Precipitation occurred during the reaction period but agitation was maintained by magnetic stirring. After the reaction period of 3 hours, thin layer chromatography (ethyl acetate/methanol/30% aqueous trimethylamine 7:2:4 v/v/v) indicated that the reaction had proceeded to an extent of 70%. The reaction mixture was allowed to cool and the precipitated solid was filtered off, washed with cold water and dried in a vacuum oven at 60° C. The solid was purified by dissolving in 600 ml. hot water, filtering and concentrating the solution to about 450 ml. It was then left to crystallise overnight. The crystalline solid was filtered off, washed with cold water and dried to constant weight in a vacuum oven at 70° C. There was obtained a first crop of 15.0 g. monosodium 4-methoxy-4'-carboxymethoxy-chalcone, thin layer chromatography of which (ethyl acetate/methanol/30% aqueous trimethylamine 7:2:4 v/v/v) showed it to be more than 99% pure; m.p. 324°–343° C.

A portion of the sodium salt was converted into the corresponding free acid for characterisation; m.p. 194°–195° C. The NMR spectrum confirmed the structure of the acid.

EXAMPLE 18

(a) A solution of 26.4 g. sodium hydroxide and 34.05 g. (20% excess) chloroacetic acid in 330 ml. distilled water was added to 49.8 g. 4-hydroxy-3-methoxyacetophenone and the resultant mixture was refluxed on an oil bath for 9 hours, with magnetic stirring. The pH was monitored at regular intervals and kept within the range of 8–9 by adding further sodium hydroxide solution. Thin layer chromatography (chloroform/methanol/acetic acid 94:5:1 v/v/v) showed that the reaction was then about 80% complete. Heating for a further 2 hours did not improve the yield. The reaction mixture was cooled, transferred to a separating funnel and washed with ethyl acetate to remove unreacted starting material. The aqueous layer was acidified with hydrochloric acid and the precipitate obtained was filtered off, washed with water until the washings were neutral and then dried in a vacuum oven at 80° C., the yield of crude product obtained being 39.89 g. It was recrystallised from methanol/ethyl acetate to give a first crop of 22.0 g. of white crystals of 4-carboxymethoxy-3-methoxyacetophenone. A second crop of 7 g. was obtained by further concentration of the mother liquor. Thin layer chromatography showed that the first crop was more than 99% pure (m.p. 153°–155° C.), whereas the second crop contained about 5% of impurities.

(b) 11.7 g. 4-Carbomethoxybenzaldehyde were dissolved in 80 ml. 10% aqueous sodium hydroxide solution and 17.92 g. 4-carboxymethoxy-3-methoxyacetophenone added thereto, while stirring magnetically. After stirring for 10 minutes at ambient temperature, a yellow solid precipitated and thin layer chromatography showed about 50% reaction. A further 1 g. 4-carboxymethoxybenzaldehyde was added and the reaction mixture further stirred for 2 hours at ambient temperature, after which time the reaction had proceeded to an extent of about 60%. 100 ml. Methanol were then added to the reaction mixture, with thorough stirring. The solid material was filtered off, washed with methanol and dried to constant weight in a vacuum oven at 80° C. to give 15.0 g. of a first crop; m.p. >300° C. A second crop of 8 g. was obtained by adding ethanol to the mother liquor. Thin layer chromatography showed that the first crop was more than 99% pure disodium 4-carboxy-4'-carboxymethoxy-3'-methoxy-chalcone, whereas the second crop was mainly impurities, identified as terephthalic acid disodium salt.

1 g. of the disodium salt was converted into the corresponding free acid by dissolving in water and acidifying with hydrochloric acid; m.p. 278°–280° C. Thin layer chromatography (ethyl acetate/aqueous trimethylamine/methanol) showed the free acid to be more than 99% pure.

EXAMPLE 19

(a) 15.2 g. 4-Hydroxy-3-methoxybenzadehyde, 19.4 g. 4-carboxymethoxyacetophenone (see Example 3) and 100 ml. 10% aqueous sodium hydroxide solution were heated at 70° C. under an atmosphere of nitrogen for 3 hours, thin layer chromatography (ethyl acetate/water/30% trimethylamine/ethanol) then indicating that no further reaction was taking place. A small amount of methanol, followed by 600 ml. ethanol was added to the reaction mixture to give a precipitate which was filtered off, washed with ethanol and dried to give 9.4 g. of a first crop. Further dilution of the mother liquor with ethanol gave 7.5 g. of a second crop. Thin layer chromatography indicated that both crops only contained a small amount of impurity. The product thus obtained was the desired disodium 4-hydroxy-3-methoxy-4'-carboxymethoxy chalcone, which had a brick-red colour.

(b) 12.0 g. of the disodium salt were dissolved in a minimum amount of water to give a deep red solution. Dilute hydrochloric acid was slowly added thereto, with stirring, until the red colour of the solution had changed to a pale orange-yellow colour. Any precipitated diacid was filtered off and the filtrate was concentrated until crystallisation occurred. The first crop of material obtained was filtered off, washed with ethanol and dried to constant weight in a vacuum oven at 100° C. the yield being 10.4 g. Thin layer chromatography (ethyl acetate/methanol/30% ethanolic trimethylamine 7:2:4 v/v/v) showed that this first crop was pure. The monosodium 4-hydroxy-3-methoxy-4'-carboxymethoxy-chalcone thus obtained had a melting point of >360° C.

EXAMPLE 20

(a) A mixture of 100 g. sodium 4-hydroxy-butanoate and 2 liters of 2% concentrated sulphuric acid in methanol was heated under reflux for 4 hours while stirring magnetically. The reaction mixture was cooled and, while stirring, sufficient sodium bicarbonate was added to increase the pH value to about 7–8. The precipitated sodium salts were filtered off and washed with 500 ml. diethyl ether, the washings being added to the original methanolic filtrate. The total organic liquids were concentrated, filtration being carried out whenever bumping occurred. After all the solvent had been removed, 65 g. of a clear pale yellow liquid remained, which was kept dry on Type 4A molecular sieve. The product was methyl 4-hydroxybutanoate.

(b) 25 g. Methyl 4-hydroxybutanoate were mixed with 47.5 g. toluene-sulphonyl chloride and 250 ml. dry pyridine at 5° C. and kept at this temperature for 17 hours, whereafter the reaction mixture was poured into 2 liters ice water. The oil thus formed was extracted with diethyl ether and the ethereal extract was washed with 500 ml. 6 N hydrochloric acid to remove excess pyridine, followed by washing with a saturated aqueous solution of sodium bicarbonate until neutral. Concentration of the organic layer gave 32.5 g. of a yellow oil which was dissolved in diethyl ether, treated with decolorising charcoal, filtered and the filtrate concentrated to give 30.5 g. of a pale yellow oil which slowly crystallised at 5° C. Thin layer chromatography (petroleum ether/dichloromethane/acetone 6:3:1 v/v/v) showed the product to be pure. The methyl 4-(p-toluene-sulphonyl)-butanoate thus obtained had a melting point of 23° C.

(c) 12.2 g. 4-Hydroxyacetophenone were reacted under anhydrous conditions with 5.8 g. sodium hydride (50% oil dispersion) in 70 ml. dimethyl formamide which had been dried over Type 4A molecular sieve. 24 g. Methyl 4-(p-toluene-sulphonyl)-butanoate in 20 ml. dry dimethyl formamide were added to the resultant solution over the course of 10 minutes. After the addition was complete, the reaction mixture was heated at 60° C. for 6 hours, whereafter thin layer chromatography (petroleum ether/dichloromethane/acetone 6:3:1 v/v/v) showed that the reaction was about 80% complete. After cooling, the pH was adjusted to 1 by the careful addition of dilute hydrochloric acid, whereafter the reaction mixture was extracted with diethyl ether. The ethereal extract was washed with a 10% aqueous sodium hydroxide solution to remove any phenolic starting material. After washing with water to remove any basic material, the ethereal solution was dried with anhydrous sodium sulphate. Solvent was then removed to give 20.5 g. of a pale brown oil which was hydrolysed by heating at 60° C. for 30 minutes with 30 ml. of a 10% aqueous sodium hydroxide solution and 30 ml. ethanol, thin layer chromatography showing that hydrolysis was complete. The reaction mixture was acidified with dilute hydrochloric acid and the precipitated solid was filtered off, washed with water and dried to constant weight in a vacuum oven at 60° C. to give 15.5 g. of product. This was crystallised from ethyl acetate/ethanol to give pale yellow crystals which were filtered off, washed with ethyl acetate and dried in a vacuum oven at 60° C. to give a first crop of 9.3 g. A second crop of 3.2 g. of yellow crystals were obtained by concentration of the mother liquors, thin layer chromatography (chloroform/methanol/acetic acid 94:5:1 v/v/v) showing both crops to be more than 99% pure. The 4-carboxy-propionoxyacetophenone thus obtained had a melting point of 154°–155° C.

(d) 12.2 g. 4-Carboxypropionoxyacetophenone were suspended in 60 ml. of a 10% aqueous sodium hydroxide solution and 8.24 g. 4-carboxybenzaldehyde added thereto. The reaction mixture was stirred for 1 hour at ambient temperature and then diluted to 250 ml. with ethanol. The precipitate obtained was filtered off, washed well with ethanol and then dried to constant weight in a vacuum oven at 70° C. 18.2 g. of pale yellow solid disodium 4-carboxy-4''-carboxypropionoxy chalcone were obtained, thin layer chromatography showing the compound to be about 98% pure. This amorphous disodium salt was dissolved in a minimum amount of hot water, the solution was filtered and ethanol was slowly added to the filtrate, with swirling. The crystalline solid formed was filtered off, washed with ethanol and dried at 70° C. in a vacuum oven to give 12.5 g. of the disodium salt; m.p. >330° C. (dec.). Thin layer chromatography (ethyl acetate/methanol/30% aqueous trimethylamine) showed the product to be more than 99% pure.

The corresponding free acid was prepared thereof in the usual manner; m.p. 261°–262° C.

EXAMPLE 21

(a) 9.0 g. 4-Carboxymethoxy-benzaldehyde (see Example 5) and 8.2 g. 4-acetylbenzoic acid were dissolved in 50 ml. 10% aqueous sodium hydroxide solution and the solution stirred at ambient temperature for 2.25 hours. 150 ml. Ethanol were added and the solid precipitate obtained was filtered off, washed with ethanol and dried to give 16.9 g. disodium 4'-carboxy-4'-carboxymethoxy chalcone. This disodium salt was converted into the acid by dissolving in water, acidifying the solution with concentrated hydrochloric acid, filtering off the solid obtained, washing with water and drying, the yield being 15.1 g. Thin layer chromatography showed the presence of about 7% of polar impurities, most of which were removed by refluxing the solid with methanol, filtering and drying the undissolved solid, the yield being 11.9 g. Thin layer chromatography then showed the product to be about 98% pure. The solid was dissolved in dimethyl formamide and the solution was filtered and evaporated to a small volume. 200 ml. Methanol was added and the solid precipitate obtained was filtered off, washed with methanol and dried to give 8.0 g. of product, thin layer chromatography of which showed it to be more than 99% pure. The 4'-carboxy-4-carboxymethoxy-chalcone thus obtained had a melting point of 312°–314° C.

(b) 14.0 g. of the diacid obtained in (a) above were slurried with 20 ml. methanol and a solution of 3.435 g. sodium hydroxide in 28 ml. distilled water added in small portions, with stirring. In order to prevent thickening and to give a final solution, it was necessary to add a further 32 ml. of distilled water. The solution was filtered and 200 ml. methanol were added to the filtrate. The precipitated solid obtained was filtered off, washed with methanol and dried to give a yield of 5.9 g. 500 ml. Ethanol were added to the filtrate to give 6.6 g. of a second crop of material which was treated in the same way as the first crop. Thin layer chromatography showed both crops to be more than 99% pure. The product thus obtained was disodium 4'-carboxy-4-carboxymethoxy-chalcone, which had a melting point of 360° C.

EXAMPLE 22

(a) 60 g. Ethyl p-toluene-sulphonate were placed in a 1 liter round-bottomed three-necked flask and 320 ml. acetic anhydride added thereto. The solution obtained was cooled to −5° C. and 50 ml. concentrated sulphuric acid slowly added thereto at such a rate that the temperature did not exceed 15° C. When all the acid had been added, the reaction mixture was cooled to −5° C. and a solution of 65 g. chromium trioxide in 300 ml. acetic anhydride slowly added at such a rate that the temperature did not rise above 4° C. After completion of the addition, the reaction mixture was left to stand for 30 minutes at 5° C. and then poured, while stirring, into 4 liters of ice/water. The green oily solution was left to stand for 12-15 hours, during which time crystallisation occurred. The solid was filtered off, taken up in 300 ml. diethyl ether and the solution washed with a 2% aqueous sodium carbonate solution until no colour was apparent in the aqueous solution, three washes being necessary. The ethereal solution was dried over anhydrous sodium sulphate and then evaporated to give 51.0 g. of crystalline solid which was shown to be pure by thin layer chromatography (petroleum ether (b.p. 60°–80° C.)/dichloromethane/acetone 6:3:1 v/v/v). This product was 4-ethyl-sulphonyl-benzal diacetate.

(b) 12.64 g. 4-Ethyl sulphonyl-benzal diacetate were placed in a 500 ml. round-bottomed flask and 100 ml. ethanol and 100 ml. 10% aqueous sulphuric acid added thereto, followed by heating for 45 minutes. The resulting brown solution was evaporated to about half its volume, whereafter 150 ml. 10% aqueous sodium hydroxide solution were added thereto. 4-Carboxymethoxyacetophenone was then added to the basic solution and the mixture agitated to ensure rapid solution. The reaction mixture was heated on a steambath for 3 hours, then cooled and 500 ml. methanol added to precipitate the product. The precipitate was filtered off with suction, sucked dry and washed five times with methanol, whereafter the filtrate was clear. Upon drying in vacuo at 110° C., there were obtained 16.8 g. of a pale yellow amorphous solid which was found to be about 90% pure by thin layer chromatography (ethyl acetate/methanol/30% aqueous trimethylamine 7:2:4 v/v/v). This product was dissolved in about 1 liter of hot water, filtered and cooled, whereupon crystallisation occurred. The crystals were filtered off, washed with cold water and dried in a vacuum oven at 110° C. to give 14.1 g. of pale yellow crystalline solid, thin layer chromatography of which (ethyl acetate/methanol/30% trimethylamine 7:2:4 v/v/v) showed it to be more than 99% pure. This product was disodium 4'-carboxymethoxy-4-sulphochalcone, which had a melting point of >360° C.

The corresponding diacid was prepared by dissolving the disodium salt in water, adding dilute hydrochloric acid and filtering off the precipitated solid. It was washed with water and dried in a vacuum oven at 100° C. The diacid had a melting point of >360° C.

EXAMPLE 23

(a) 30.4 g. 3-Methoxy-4-hydroxybenzaldehyde were dissolved in 120 ml. dimethyl formamide and 9.2 g. sodium hydride (50% dispersion in oil) slowly added, with stirring, to the resultant solution, more dimethyl formamide being added to keep the reactants in solution. After cooling the reaction mixture to ambient temperature, a solution of 24.6 g. ethyl chloroacetate in dimethyl formamide was added and stirring continued at ambient temperature for 3 days, whereafter thin layer chromatography (petroleum ether(b.p. 60°–80° C.)/dichloromethane/acetone 6:3:1) indicated that the reaction was at least 85% complete. The reaction mixture was then acidified with dilute hydrochloric acid, followed by extraction with diethyl ether. The organic extract was washed once with 500 ml. 10% aqueous sodium hydroxide solution and 3 times with 300 ml. amounts of distilled water, followed by drying over anhydrous sodium sulphate. The solvent was removed and the yellow solid obtained was washed with petroleum ether to remove any oil from the sodium hydride dispersion. The solid was then dried to constant weight in a vacuum desiccator to give 22.4 g. 4-carbethoxymethoxy-3-methoxybenzaldehyde; m.p. 65°–66.5° C. Thin layer chromatography indicated that the product was more than 99% pure.

(b) 15.4 g. 4-Carbethoxymethoxy-3-methoxybenzaldehyde and 56 ml. 10% aqueous sodium hydroxide solution were mixed and 15 ml. methanol added thereto. Water was then added until a clear solution was obtained. 4-Carboxymethoxyacetophenone (see Example 3) was added to this solution and the reaction mixture left to stand overnight. A further 10 ml. 10% aqueous sodium hydroxide solution was added to keep the reaction mixture alkaline. After a further 24 hours at ambient temperature, thin layer chromatography (ethyl acetate/methanol/30% aqueous trimethylamine 7:2:4 v/v/v) showed that the reaction had proceeded to about 85%. The reaction mixture was then introduced into a conical flask and diluted with ethanol until precipitation occurred. The precipitate was filtered off, washed well with ethanol and dried to constant weight in a vacuum oven, the yield being 22.8 g. Thin layer chromatography indicated that the product was about 95% pure. It was crystallised from methanol/water to give a first crop of 19.5 g. of material which was over 99% pure after drying to constant weight in a vacuum oven at 80° C. The product had a melting point of >360° C. (decomposition from 240° C.). It was disodium 4,4'-di-(carboxymethoxy)-3-methoxychalcone.

A sample of this disodium salt was converted into the corresponding diacid by acidifying an aqueous solution thereof with dilute hydrochloric acid, filtering off the precipitate obtained, washing it with water and drying in a vacuum oven at 80° C. The diacid thus obtained had a melting point of 210°-211° C. (decomp.).

The disodium salt was also converted into the corresponding dimethyl ester in the following manner: 20 mg. of the disodium salt and 2 drops of acetic acid were mixed with 1 ml. dimethyl sulphoxide and a solution obtained by warming. After cooling, excess diazomethane was added and, after completion of the reaction, unreacted diazomethane was destroyed by adding a drop of acetic acid. The dimethyl ester obtained after working up the reaction mixture was found to be 99% pure.

EXAMPLE 24

1.64 g. 4-Acetylbenzoic acid and 1.50 g. 4-carboxybenzaldehyde were added to a solution of 1.0 g. sodium hydroxide and 20 ml. 90% aqueous ethanol. The reaction mixture was stirred under reflux for 2 hours and the solid was filtered off, washed thoroughly with ethanol and dried. The yield was 2.1 g. Thin layer chromatography (ethyl acetate/methanol/30% aqueous trimethylamine 7:2:4 v/v/v) showed the material to be about 80% of the desired product. This was purified by column chromatography through silica gel to give 1.10 g. of disodium 4,4'-dicarboxychalcone of 99% purity. It had a melting point greater than 360° C.

A sample of this disodium salt was converted in the usual manner into the corresponding free acid, which also had a melting point greater than 360° C.

The present invention also includes within its scope pharmaceutical compositions containing at least one of the new compounds according to the present invention, in admixture with a solid or liquid pharmaceutical carrier.

Solid compositions for oral administration include compressed tablets, pills, dispersible powders and granules. In such solid compositions, one of the new compounds is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavouring agents.

The compositions according to the present invention, for oral administration, include capcules of absorbable material, such as gelatine, containing one of the new derivatives, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The compositions according to the present invention for topical application include lotions, creams, pastes, ointments and liniments.

The percentage of active material in the compositions of the present invention may be varied, it being necessary that it should constitute a proportion such that a suitable dosage for the desired therapeutic effect shall be obtained. In general, the preparations of the present invention should be administered orally or parenterally to humans to give 1 to 1000 mg. and preferably 10-500 mg. of active substance per day.

The following Examples illustrate pharmaceutical compositions according to the present invention:

EXAMPLE 25

250 mg. tablets are prepared containing:

| | |
|---|---|
| 3-carboxy-4'-hydroxychalcone | 50 mg. |
| starch | 100 mg. |
| lactose | 95 mg. |
| magnesium stearate | 5 mg. |

EXAMPLE 26

500 mg. tablets are prepared containing:

| | |
|---|---|
| disodium 4,4'-dicarboxychalcone | 100 mg. |
| starch | 150 mg. |
| lactose | 240 mg. |
| magnesium stearate | 10 mg. |

EXAMPLE 27

500 mg. tablets are prepared containing:

| | |
|---|---|
| disodium 4-carboxy-3'-fluoro-4'-carboxymethoxychalcone | 100 mg. |
| starch | 190 mg. |
| lactose | 200 mg. |
| magnesium stearate | 10 mg. |

The compositions according to Examples 25 to 27 are intended for oral administration to humans for treating inflammatory and allergic conditions and for treating ulcerous conditions of the gastro-intestinal tract.

We claim:

1. A compound of the general formula:

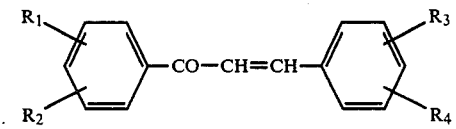

wherein $R_1$ is a carboxyalkoxy radical, $R_2$ and $R_3$, which may be the same or different, are hydrogen or halogen atoms, hydroxyl groups or alkoxy radicals and $R_4$ is carboxylalkoxy or a carboxyalkylcarbonyloxyalkyl radical or a carboxylic acid group; and the non-toxic inorganic and organic salts thereof.

2. A compound according to claim 1, which is 4-carboxy-4'-carboxymethoxylchalcone.

3. A compound according to claim 1, which is 4,4'-di(carboxymethoxy)-chalcone.

4. A compound according to claim 1, which is 3-carboxy-4'-carboxymethoxychalcone.

5. A compound according to claim 1, which is 4-carboxy-3'-fluoro-4'-carboxymethoxychalcone.

6. A compound according to claim 1, which is 4'-carboxy-methoxy-4β-carboxypropionyloxymethylchalcone.

7. A compound according to claim 1, which is 4-carboxy-3'-carboxymethoxychalcone.

8. A compound according to claim 1, which is 2-carboxy-4'-carboxymethoxychalcone.

9. A compound according to claim 1, which is 3,4'-di(carboxymethoxy)-chalcone.

10. A compound according to claim 1, which is 4-carboxy-4'-carboxymethoxy-3'-methoxychalcone.

11. A compound according to claim 1, which is 4-carboxy-4'-carboxypropionoxychalcone.

12. A compound according to claim 1, which is 4,4'-di(carboxymethoxy)-3-methoxychalcone.

13. A pharmaceutical composition for treating inflammatory and allergic conditions and for treating ulcerous conditions of the gastro-intestinal tract in humans which comprises an effective amount of a compound of claim 1 in admixture with a solid or liquid pharmaceutical diluent or carrier.

* * * * *